(12) United States Patent
Frank

(10) Patent No.: US 6,454,754 B1
(45) Date of Patent: Sep. 24, 2002

(54) RESPIRATORY INFECTION TREATMENT DEVICE

(76) Inventor: Steven R. Frank, 11192 Twin Spruce Rd., Golden, CO (US) 80403

( * ) Notice: Subject to any disclaimer, the term of this patent is extended or adjusted under 35 U.S.C. 154(b) by 0 days.

(21) Appl. No.: 09/718,520

(22) Filed: Nov. 21, 2000

Related U.S. Application Data

(63) Continuation of application No. 09/182,581, filed on Oct. 29, 1998, now abandoned.

(51) Int. Cl.[7] ............................................. A61N 31/00
(52) U.S. Cl. ........................................ 604/500; 604/19
(58) Field of Search ................ 604/19, 20, 21, 604/48, 500, 43.01; 128/200.14; 424/45

(56) References Cited

U.S. PATENT DOCUMENTS

| | | |
|---|---|---|
| 3,831,598 A | 8/1974 | Tice |
| 3,918,459 A | 11/1975 | Horn |
| 3,964,477 A | 6/1976 | Ellis et al. |
| 4,305,390 A | 12/1981 | Swartz |
| 4,411,648 A | 10/1983 | Davis et al. |
| 4,474,570 A | 10/1984 | Ariura et al. |
| 4,774,833 A | 10/1988 | Weibler et al. |
| 4,821,700 A | 4/1989 | Weibler et al. |
| 5,306,287 A | 4/1994 | Becker |
| 5,322,520 A | 6/1994 | Milder |
| 5,328,451 A | 7/1994 | Davis et al. |
| 5,498,248 A | 3/1996 | Milder |
| 5,571,149 A | 11/1996 | Liss et al. |
| 5,639,441 A * | 6/1997 | Sievers et al. ......... 128/200.23 |
| 5,676,648 A | 10/1997 | Henley |
| 5,749,845 A | 5/1998 | Hildebrand et al. |
| 5,785,972 A * | 7/1998 | Tyler ........................ 424/539 |
| 5,846,217 A | 12/1998 | Beck et al. |
| 5,865,787 A | 2/1999 | Shapland et al. |
| 6,001,088 A | 12/1999 | Roberts et al. |
| 6,095,134 A * | 8/2000 | Sievers et al. ......... 128/200.14 |

* cited by examiner

Primary Examiner—Brian L. Casler
Assistant Examiner—Jeremy Thissell
(74) Attorney, Agent, or Firm—Emery L. Tracy

(57) ABSTRACT

A device for treating an illness or infection in the respiratory tract of a body is provided. The device administers an antimicrobial mist, which coats the tissues in the respiratory tract where the infection is colonizing.

4 Claims, 1 Drawing Sheet

RESPIRATORY INFECTION TREATMENT DEVICE

Figure 1:
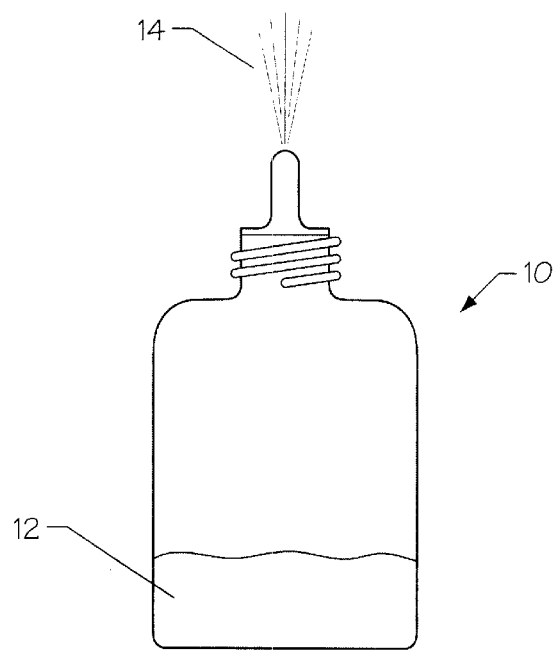

The present application is a continuation of patent application Ser. No. 09/182,581, filed on Oct. 29, 1998, entitled "Electrolytic Substance Infusion Device" now abandoned.

BACKGROUND OF THE INVENTION

1. Field of the Invention

This invention relates generally to a treatment device for respiratory infections, more particularly, it relates to a treatment device which delivers metal colloids into the upper and lower respiratory tracts in a manier which terminates viral and bacterial respiratory infections by coating the infected tissues with antimicrobial metal colloids.

2. Description of the Prior Art

There are a number of viral and bacterial infections, which gain entry to the body and subsequently thrive in the moist and well-vascularized membranes of the nasal passageway, the sinuses and the lungs. Presently, when these infections occur, the infected party is prescribed systemic doses of antibiotics or antiviral agents. These agents are most often ingested in quantities of several grams per day in order to achieve the required systemically diluted tissue densities of thirty (30) to fifty (50) micrograms per milliliter.

The unfortunate consequence of this dosing is that in the case of antivirals, a large number of liver cells or kidney cells will be damaged. When the agent is an antibiotic, the natural fauna of bacteria through out the body is dramatically altered allowing opportunistic bacteria to over-load an area and often resulting in secondary infections in other areas or fungal infections. Indeed, when a therapeutic agent that is intended to operate in the nose, sinuses or lungs is required to be administered systemically, the required dose and body-burden is quite large.

Often times, the infection being treated does not respond to the first antibiotic treatment and multiple courses of various antibiotics are sequentially administered further burdening the body and detrimentally distorting the natural bacterial balance. This usually leads to prolonged feelings of malaise for the treated subject and peripheral ailments such as yeast infections, low energy and diarrhea.

The treatment of respiratory infections by means of an appropriate delivery of a silver colloid to the infected tissue overcomes both of the problems of the currently administered protocol by dramatically reducing the amount of the anti-microbial required and by administering it directly to the infected tissue.

Presently, silver colloids are utilized occasionally to treat infections but the protocolsand administration mechanisms are usually a medicine dropper or a teaspoon. The method utilized is to "drink" a small amount (a teaspoon) of silver colloid. This results in a systemic dilution of ionic silver on the order of nanograms per milliliter of tissue throughout the entire body. Additionally, the commercially available preparations tend to be of concentrations too low to be effective. They tend to be on the order of less than 10 ppm. This use protocol results in tissues densities on the order of nanograms per milliliter. Laboratory studies have shown for years that this level of concentration in infected tissue has no measurable antimicrobial effects.

SUMMARY

The present invention is a means and protocol for treating an illness or infection of respiratory tissue of a body. The device consists of either a nebulizer or spray means for making a mist of appropriately sized droplets of fluid. This fluid consists of the appropriate concentration of pure silver colloid. The means requires administration of this colloid with these mechanical dispensing mechanisms according to the prescribed replenishment protocol. The result is to maintain a ten (10) microgram or greater concentration of ionic silver (a known antimicrobial) or other ionically suspended metal in the infected tissue. This is a highly effective means of dispatching disease without subjecting the entire body to a high level of toxic antiviral pharmacological agents or antibiotics.

The administration of ionic silver colloid in this manner makes it possible to more effectively treat an infection with 10,000 times less antimicrobial agent than currently prescribed techniques or tools require. The results seen have surpassed the efficacy of both pharmaceutical antivirals and antibiotics on sinus infections and lower respiratory infections. The effectiveness of this therapy on the common cold has produce results far better than any other known treatment typically terminating a cold in twelve (12) to twenty-four (24) hours when used at the first signs of infection.

In this manner, it represents a quantum leap in the treatment of respiratory illnesses. It utilizes a benign substance (silver colloid) to effectively treat major infections and yields no observable adverse side effects. An additional benefit of this invention is that since the treatment is so benign to the subject, it can be used prophylactically. When a person is being exposed to an environment of contagious airborne microbes, they can use the nasal spray regularly to dispatch the inhaled infectious germs before they can multiply sufficiently to overcome the immune systems and produce a symptomatic illness. This level of preventative therapy has never before been available against airborne infectious disease.

Antimicrobial is used to indicate anti-viral, anti-fungal and anti-bacterial. Although the inventor has used silver colloid in the majority of the tests, copper colloids have showed significant anti-fungal properties as well.

BRIEF DESCRIPTION OF THE DRAWINGS

FIG. 1 is a side view illustrating a nasal spray bottle embodiment of present invention, constructed in accordance with the present invention, for treatment of colds and sinus infections; and FIG. 2 is a side view illustrating a nebulizer embodiment of the present invention, constructed in accordance with the present invention, for treating respiratory ailments and infections of the lower respiratory tract.

DETAILED DESCRIPTION OF THE PREFERRED EMBODIMENTS

In the nasal spray bottle 10 of the present invention, as illustrated in FIG. 1, the agent 12 (typically twenty (20) ppm aqueous silver colloid) is dispensed by the user squeezing the nasal spray bottle when it is placed within the nasal passageway (not shown) of a user (not shown). The action of dispensing the agent 12, accompanied by an inhalation of the user, coats the nasal passageways with the agent 12 thereby rendering the nasal passageways antiseptic.

In the nebulizer 20 of the present invention, as illustrated in FIG. 2, the agent 22 (typically forty (40) to sixty (60) ppm aqueous silver colloid) is placed in the nebulizer chamber 24. The nebulizer 20 then produces droplets of less than ten (10) microns in diameter, which are inhaled by the user receiving therapy. The small droplets of agent 22 are able to negotiate the pharyngeal bends without significant impact loss and coat the bronchi of the lungs where some airborne virus and bacteria colonize, thereby terminating the infection.

VARIOUS PREFERRED EMBODIMENTS OF THE PRESENT INVENTION

Nasal Spray Device

As illustrated in FIG. 1, a manner of treating colds and sinus infections when they reside primarily in the upper respiratory regions such as the sinuses and the nasal passages ways. This embodiment utilizes atomizing spray bottles 10, which produce a mist 14. This mist 14 is inhaled through the nose of the user every fifteen (15) to sixty (60) minutes. The mist 14 is comprised of a colloidal suspension of silver such as a twenty (20) ppm aqueous silver colloid. The mist spray 14 is comprised of droplets large enough so that they predominantly contact the nasal membranes and coat the passages ways therein. The colloidal suspension migrates into the sinus passages where it kills bacteria. In the nasal passageways, it serves to terminate viral infections such as colds.

The means of this invention is to utilize either a nasal spray bottle 10 or a nebulizer to produce small airborne droplets 14 of silver colloid in high enough concentration so that when inhaled, they coat the tissues where the infection is propagating. In the case of treating colds, the nasal spray bottle 10 delivers a sufficiently small droplet mist and is convenient to use. By administering the twenty (20) ppm pure silver colloid directly to the nasal passageway, where the virus is multiplying, a sufficiently high tissue concentration (greater than ten (>10) micrograms/ml) is maintained only in the area of the infection dramatically reducing amount of agent required.

Nebulizer Device

Figure 2:
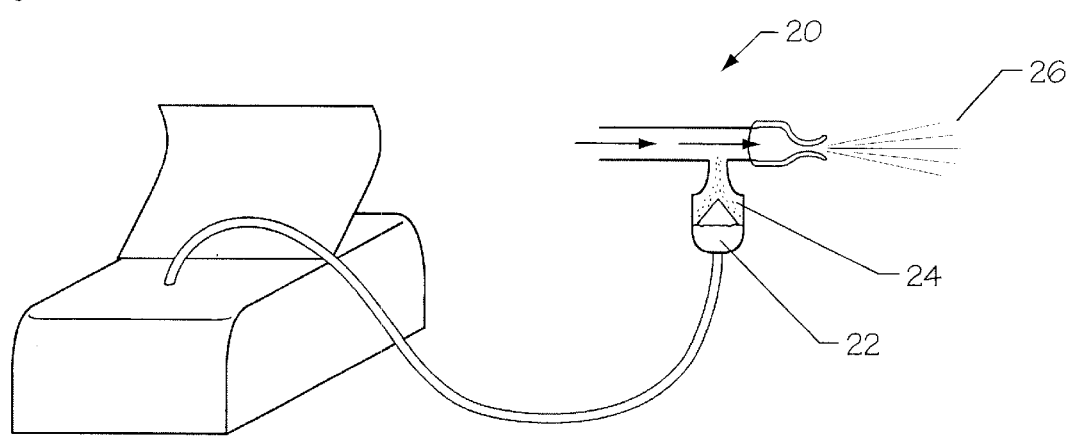

As illustrated in FIG. 2, a manner of treating microbial infections, which have already reached the lungs or the throat, is provided. In this embodiment, the infusion or nebulizer device 20 of the present invention includes nebulizer device 20 having a colloidal suspension preparation 22 containing ionic silver within a carrier, e.g., water. The colloidal suspension 22 generally of forty (40) to sixty (60) ppm silver is administered with an ultrasonic nebulizer, aerosol, or spray atomizer 24 to combat infections of the lungs such as bronchitis, chest colds, anthrax, and tuberculosis, for instance. By propelling the colloidal suspension 22 of the silver in this nebulized flow of moist air, any tissue that can be reached and infected by airborne virus can also be reached by the antimicrobial agent. The nebulizer device 20 provides small droplet size mist 26, typically less than ten (10) microns, which can negotiate the pharyngeal pathway and reach the lower respiratory tract. Inhalation through the nose can allow treatment of the nasal passageways and has been shown to eliminate colonization of cold virus and even overcoming severe sinus infections.

Some silver colloids are held in higher suspensions by means of attaching the silver ions to proteins. These are called "mild silver proteins". It is unfortunate that the very process of binding the ions to the proteins to increase the available concentration also reduces the effectiveness by rendering the ions less bioactive. In fact, the achieved higher concentrations (typically two hundred and fifty (250 ppm)) are less effective than the twenty (20)ppm pure silver colloids tested by the inventor. It is important to use twenty (20)ppm or greater pure silver colloids to achieve enough antimicrobial activity when diluted by body fluids such as mucus and interstitial fluids. For lower respiratory infections where the surface area of the lungs is very large and there is plenty of fluid, concentrations of forty (40) to sixty (60) ppm pure silver colloid are required. Since mucosal flow will carry the inhaled coating of silver colloid away in less than an hour, a critical part of the process, which has not been practiced, is the appropriate re-administration protocol. It is necessary to replenish the area of infected tissue with the administration of more colloid at a regular interval designed to maintain the required level of tissue density in order to maintain regional antisepsis. For colds and sinus infections, the nasal aspiration should be repeated every thirty (30) to sixty (60) minutes in order for the therapy to be effective. For lower respiratory infections the nebulized inhalation should be administered for three (3) to five (5) minutes every few hours.

Thus, the droppletized application of the twenty (20) to sixty (60) ppm concentration at the correct replenishment interval provides for a highly effective means of terminating a viral or bacterial infection of tissues in the respiratory tract. This has demonstrated far greater effectiveness than any current therapy for colds, sinus infections and lower respiratory infections.

The foregoing exemplary descriptions and the illustrative preferred embodiments of the present invention have been explained in the drawings and described in detail, with varying modifications and alternative embodiments being taught. While the invention has been so shown, described and illustrated. it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements, which are disclosed herein.

What is claimed is:

1. A method of infusing a colloidally suspended antimicrobial substance into tissue of a body, the method comprising:

providing a misting device;

providing an antimicrobial substance of colloidal silver suspension within the misting device having a concentration of colloidal silver suspension between approximately twenty (20) ppm and approximately sixty (60) ppm;

ejecting the antimicrobial substance in a mist of small droplets;

delivering the colloidal silver suspension in a coating into the upper and lower respiratory tract achieving predetermined antimicrobial concentrations in the infected tissues; and further delivering the antimicrobial concentrations every thirty (30) to sixty (60) minutes to maintain an effective antimicrobial effect in environments of high fluid flushing.

2. The method of claim 1 and further comprising using a nebulizer to achieve the small droplets necessary to reach the lower respiratory tract.

3. The method of claim 2 and further comprising a nasal spray bottle to achieve the larger droplets necessary to coat the nasal passage ways.

4. The method of claim 2 and further comprising a nasal spray coating to allow migration of the agent into the sinus cavities for treatment of sinus infections.

* * * * *